United States Patent
Gañan-Cálvo

(10) Patent No.: US 6,394,429 B2
(45) Date of Patent: *May 28, 2002

(54) DEVICE AND METHOD FOR FLUID AERATION VIA GAS FORCED THROUGH A LIQUID WITHIN AN ORIFICE OF A PRESSURE CHAMBER

(75) Inventor: Alfonso Gañan-Cálvo, Seville (ES)

(73) Assignee: Universidad de Sevilla, Seville (ES)

( * ) Notice: Subject to any disclaimer, the term of this patent is extended or adjusted under 35 U.S.C. 154(b) by 0 days.

This patent is subject to a terminal disclaimer.

(21) Appl. No.: 09/932,225

(22) Filed: Aug. 17, 2001

Related U.S. Application Data

(63) Continuation of application No. 09/604,834, filed on Jun. 27, 2000, now Pat. No. 6,299,145, which is a continuation of application No. 09/191,756, filed on Nov. 13, 1998, now Pat. No. 6,196,525, which is a continuation-in-part of application No. 09/171,518, filed on Apr. 21, 1999, now Pat. No. 6,119,953, which is a continuation-in-part of application No. 09/192,091, filed on Nov. 13, 1998, now Pat. No. 6,116,516.

(30) Foreign Application Priority Data

| May 13, 1996 | (ES) | ............................................ 9601101 |
| Feb. 18, 1997 | (ES) | ................................ PCT/ES97/00034 |
| Dec. 17, 1997 | (ES) | ............................................ 9702654 |

(51) Int. Cl.⁷ ................................................. B01F 3/04
(52) U.S. Cl. ............................... 261/77; 261/DIG. 26; 261/DIG. 75; 426/474
(58) Field of Search .................... 261/76, 77, DIG. 26, 261/DIG. 75; 426/474, 477; 516/10

(56) References Cited

U.S. PATENT DOCUMENTS

| 3,700,170 A | 10/1972 | Blanka et al. |
| 3,804,255 A | 4/1974 | Speece |
| 3,927,152 A * | 12/1975 | Kyrias ........................ 261/122 |
| 4,141,055 A | 2/1979 | Berry et al. |
| 4,162,282 A | 7/1979 | Fulwyler et al. |
| 4,347,935 A | 9/1982 | Merrill |
| 4,352,789 A | 10/1982 | Thiel |
| 4,363,446 A | 12/1982 | Jaeggle et al. |
| 4,444,961 A | 4/1984 | Timm |
| 4,603,671 A | 8/1986 | Yoshinaga et al. |

(List continued on next page.)

FOREIGN PATENT DOCUMENTS

| CH | 563807 | 7/1975 |
| DE | 4031262 A1 | 4/1992 |
| EP | 0 249 186 A1 | 12/1987 |

(List continued on next page.)

OTHER PUBLICATIONS

Bowden et al., Science 276:233–5 (1997).
Brenn et al., *Chemical Engineering Science*, 52(2):237–244 (Jan. 1997) (Abstract).

(List continued on next page.)

Primary Examiner— Robert A. Hopkins
(74) Attorney, Agent, or Firm—Karl Bozicevic; Bozicevic, Field & Francis LLP

(57) ABSTRACT

The present invention provides aeration methods using spherical gas bubbles having a size on the order of 0.1 to 100 microns in size. A device of the invention for producing a monodispersion of bubbles includes a source of a stream of gas which is forced through a liquid held under pressure in a pressure chamber with an exit opening therein. The stream of gas surrounded by the liquid in the pressure chamber flows out of an exit orifice of the chamber into a liquid thereby creating a monodispersion of bubbles with substantially uniform diameter. The bubbles are small in size and produced with a relatively small amount of energy relative to comparable systems. Applications of the aeration technology range from oxygenating sewage with monodispersions of bubbles to oxygenation of water for fish maintenance.

24 Claims, 5 Drawing Sheets

U.S. PATENT DOCUMENTS

Figure 1A:
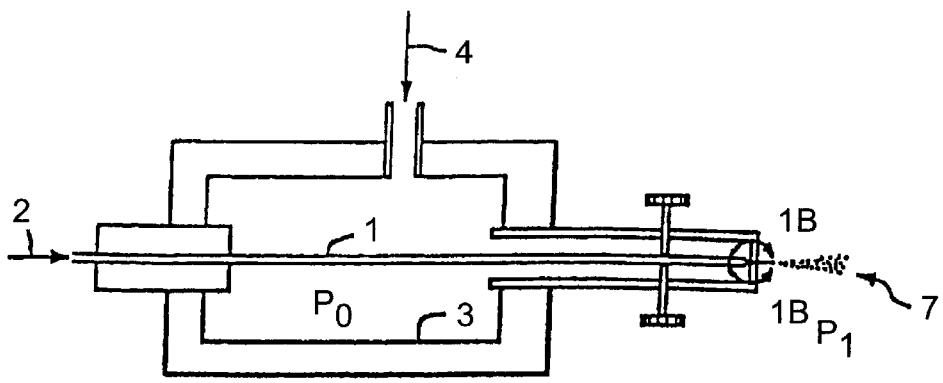

| | | |
|---|---|---|
| 4,617,898 A | 10/1986 | Gayler |
| 4,628,040 A | 12/1986 | Green et al. |
| 4,662,338 A | 5/1987 | Itoh et al. |
| 4,717,049 A | 1/1988 | Green et al. |
| 4,781,968 A | 11/1988 | Kellerman |
| 4,917,857 A | 4/1990 | Jaeckel |
| 5,020,498 A | 6/1991 | Linder et al. |
| 5,077,176 A | 12/1991 | Baggio et al. |
| 5,087,292 A | 2/1992 | Garrido |
| 5,174,247 A | 12/1992 | Tosa et al. |
| 5,180,465 A | 1/1993 | Seki et al. |
| 5,194,915 A | 3/1993 | Gilby |
| 5,230,850 A | 7/1993 | Lewis |
| 5,364,632 A | 11/1994 | Benita et al. |
| 5,364,838 A | 11/1994 | Rubsamen |
| 5,372,867 A | 12/1994 | Hasegawa et al. |
| 5,397,001 A | 3/1995 | Yoon et al. |
| 5,404,871 A | 4/1995 | Goodman et al. |
| 5,458,292 A | 10/1995 | Hapeman |
| 5,522,385 A | 6/1996 | Lloyd et al. |
| 5,554,646 A | 9/1996 | Cook et al. |
| 5,597,491 A | 1/1997 | Winkler |
| 5,697,341 A | 12/1997 | Ausman et al. |
| 5,740,794 A | 4/1998 | Smith et al. |
| 5,775,320 A | 7/1998 | Patton et al. |
| 5,961,895 A * | 10/1999 | Sanford ..................... 216/36.1 |

FOREIGN PATENT DOCUMENTS

| | | |
|---|---|---|
| EP | 0 250 164 A2 | 12/1987 |
| GB | 2255291 A | 11/1992 |
| GB | 2099078 A | 12/1992 |
| JP | 59174561 A | 10/1984 |
| JP | 03169331 | 7/1991 |
| WO | WO 90/05583 | 5/1990 |
| WO | WO 91/18682 | 12/1991 |
| WO | WO 94/11116 | 5/1994 |
| WO | WO 94/23129 | 10/1994 |
| WO | WO 95/23030 | 8/1995 |
| WO | WO 96/16326 | 5/1996 |
| WO | WO 97/43048 | 11/1997 |
| WO | WO 97/44080 | 11/1997 |

OTHER PUBLICATIONS

Borchardt et al., *Chemistry & Biology*, 4(12):961–968 (1997).

Chin et al., *Trans. ASME J. Eng. Gas Turbines Power*, 106:639–644 (1983).

Cloupeau et al. (1989), *J. Electrostat* 22:135–159.

Fernández de la Mora et al. (1994), *J. Fluid Mech.* 260:155–184.

Forbes et al., *J. Austral. Math. Soc. Ser. B.*, 32:231–249 (1990).

Gañán–Calvo et al. (1997), *J. Aerosol Sci.* 28:249–275.

Gauthier, *Optics & Laser Technology*, 29(7):389–399 (Oct. 1997).

Hartman et al. (1997), "Electrohydrodynamic Atomization in the Cone–Jet Mode," Paper presented at the ESF Workshop on Electrospray, Sevilla, Feb. 28–Mar. 1 1997 [see also the papers contained in the Special Issue for Electrosprays (1994)].

Huck et al., *Journal of American Chemical Society* pp. 8267–8268 (1998).

Jasuja, *ASME Paper* 82–GT–32 (1982).

Liu et al. (1974), *J. Coloid Interface Sci.* 47:155–171.

Lorenzetto et al., *AIAA J.*, 15:1006–1010 (1977).

Nukiyama et al., *Trans. Soc. Mech. Eng. Jpn.*, 5:68–75 (1939).

Lord Rayleigh (1879), *Proc. London Math. Soc.* 10:4–13.

Service et al., (1997), *Science*, 277:1199–1200.

Singler et al., *Phys. Fluids A*, 5:1156–1166 (1993).

Tuck et al., *J. Austral. Math. Soc. Ser. B.*, 25:433–450 (1984).

Ünal, *Metall. Trans. B.*, 20B:613–622 (1989).

Whitesides et al., *Science* 254:1312–9 (1991).

Wigg, *J. Inst. Fuel*, 27:500–505 (1964).

Winfree et al., *Nature*, 394539–44 (1998).

* cited by examiner

DEVICE AND METHOD FOR FLUID AERATION VIA GAS FORCED THROUGH A LIQUID WITHIN AN ORIFICE OF A PRESSURE CHAMBER

CROSS REFERENCES

This application is a continuation of application Ser. No. 09/604,834, filed Jun. 27, 2000 now U.S. Pat. No. 6,299,145 issued Oct. 9, 2001 which is a continuation of application Ser. No. 09/191,756 filed Nov. 13, 1998 now U.S. Pat. No. 6,196,525 issued Mar. 6, 2001 which application is a continuation-in-part of U.S. application Ser. No. 09/171,518, filed Apr. 21, 1999 now U.S. Pat. No. 6,119,953 issued Sep. 19, 2000; which application is a continuation-in-part of U.S. application Ser. No. 09/192,091, filed Nov. 13, 1998 now U.S. Pat. No. 6,116,516 issued Sep. 12, 2000; which is a national stage entry of PCT Application Serial No. PCT/ES97/00034, filed Feb. 18, 1997.

FIELD OF THE INVENTION

The invention relates generally to the field of small particle formation and more specifically to fields where it is important to create gas bubbles which are very small and uniform in size.

BACKGROUND OF THE INVENTION

Monodispersed sprays of droplets of micrometric size have attracted the interest of scientist and engineers because of their potential applications in many fields of science and technology. Classifying a polydispersed aerosol (for example, by using a differential mobility analyzer, B. Y. Liu et al. (1974), "A Submicron Standard and the Primary Absolute Calibration of the Condensation Nuclei Counter," *J. Coloid Interface Sci.* 47:155–171 or breakup process of Rayleigh's type of a capillary microjet Lord Rayleigh (1879), "On the instability of Jets," *Proc. London Math. Soc.* 10:4–13, are the current methods to produce the monodispersed aerosols of micrometric droplets needed for such applications. The substantial loss of the aerosol sample during the classification process can severely limit the use of this technique for some applications. On the other hand, although in the capillary break up the size distribution of the droplets can be very narrow, the diameter of the droplets is determined by the jet diameter (approximately twice the jet diameter). Therefore, the generation and control of capillary microjets are essential to the production of sprays of micrometric droplets with very narrow size distribution.

Capillary microjets with diameters ranging from tens of nanometers to hundred of micrometers are successfully generated by employing high electrical fields (several kV) to form the well-known cone-jet electrospray. Theoretical and experimental results and numerical calculations on electrosprays can be obtained from M. Cloupean et al. (1989), "Electrostatic Spraying of Liquids in Cone Jet Mode," *J. Electrostat* 22:135–159, Fernández de la Mora et al. (1994), "The Current Transmitted through an Electrified Conical Meniscus," *J. Fluid Mech.*260: 155–184 and Loscertales (1994), A. M. Gañán-Calvo et al. (1997), "Current and Droplet Size in the Electrospraying of Liquids: Scaling Laws," *J. Aerosol Sci.* 28:249–275, Hartman et al. (1997), "Electrohydrodynamic Atomization in the Cone-Jet Mode," Paper presented at the ESF Workshop on Electrospray, Sevilla, Feb. 28–Mar. 1, 1997 among others [see also the papers contained in the Special Issue for Electrosprays (1994)]. In the electrospray technique the fluid to be atomized is slowly injected through a capillary electrified needle. For a certain range of values of the applied voltage and flow rate an almost conical meniscus is formed at the needle's exit from whose vertex a very thin, charged jet is issued.

The jet breaks up into a fine aerosol of high charged droplets characterized by a very narrow droplet size distribution. Alternatively, the use of purely mechanical means to produce capillary microjets is limited in most of applications for several reasons: the high-pressure values required to inject a fluid through a very narrow tube (typical diameters of the order of few micrometers) and the easy clogging of such narrow tubes due to impurities in the liquid.

The present invention provides a new technique for producing uniform sized monodispersion of gas bubbles based on a mechanical means which does not present the above inconveniences and can compete advantageously with electrospray atomizers. The jet diameters produced with this technique can be easily controlled and range from below one micrometer to several tens of micrometers.

SUMMARY OF THE INVENTION

The present invention provides aeration methods using spherical gas bubbles having a size on the order of 0.1 to 100 microns in size. A device of the invention for producing a monodispersion of bubbles includes a source of a stream of gas which is forced through a liquid held under pressure in a pressure chamber with an exit opening therein. The stream of gas surrounded by the liquid in the pressure chamber flows out of an exit orifice of the chamber into a liquid thereby creating a monodispersion of bubbles with substantially uniform diameter. The bubbles are small in size and produced with a relatively small amount of energy relative to comparable systems. Applications of the aeration technology range from oxygenating sewage with monodispersions of bubbles to oxygenation of water for fish maintenance.

BRIEF DESCRIPTION OF THE DRAWINGS

FIG. 1 is a schematic view showing the basic components of one embodiment of the invention with a cylindrical feeding needle as a source of formulation.

FIG. 2 is a schematic view of another embodiment of the invention with two concentric tubes as a source of formulation.

FIG. 3 is a schematic view of yet another embodiment showing a wedge-shaped planar source of formulation. FIG. 3*a* illustrates a cross-sectional side view of the planar feeding source and the interaction of the fluids. FIG. 3*b* show a frontal view of the openings in the pressure chamber, with the multiple openings through which the atomizate exits the device. FIG. 3*c* illustrates the channels that are optionally formed within the planar feeding member. The channels are aligned with the openings in the pressure chamber.

FIG. 4 is a schematic view of a stable capillary microjet being formed and flowing through an exit opening to thereafter form a monodisperse aerosol.

FIG. 5 is a graph of data where 350 measured values of $d_j/d_o$ versus $Q/Q_o$ are plotted.

FIG. 6 is a micrograph showing the even dispersement and uniform size of air bubbles created using the method of the invention after expulsion into an aqueous solution.

DETAILED DESCRIPTION OF PREFERRED EMBODIMENTS

Before the present aeration device and method are described, it is to be understood that this invention is not limited to the particular components and steps described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "and," and "the" include plural referents unless the context clearly dictates otherwise. Thus, for example, reference to "a bubble" includes a plurality of bubbles and reference to "a gas" includes reference to a mixture of gases, and equivalents thereof known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The terms "bubble", "dispersion of bubbles" and "monodispersion of bubbles" are used interchangeably herein and shall mean small uniformly sized particles of a gas or gaseous formulation that has been dispersed using the device and method of the invention. The particles are generally spherical, and may be comprised of one or more gases or layers of gases.

The terms "air", "particle free air" and the like, are used interchangeably herein to describe a volume of air which is substantially free of other material and, in particular, free of particles intentionally added such as particles of formulation. Air is a mixture of various gas components that, may, of course vary, but usually the air will contain approximately 21% oxygen by volume. Air may also contain gases or other air-borne particles. For use in the invention, air may be filtered or treated to remove all unwanted particulate or gaseous matter, or the air may be used in an unfiltered state. Air is the preferred gas for use of the invention in oxygenation of aqueous fluids, e.g. water.

The terms "gas" and "gas formulation" as used herein refer to any gas or gaseous mixture which is desired to be dispersed using the method of the invention. For example, the formulation may be comprised of air, either filtered or unfiltered. Gases such as air may be spiked with a particular gas, such as the spiking of air with additional $0_2$ gas for use in oxygenation. A gaseous formulation may also contain suspended particlulate matter dispersed within the gas. The gas can be CO2 to carry out the carbonation of beverages (e.g. water, colas) or a gas containing an unwanted contaminant, e.g. radioactivity or an environmental toxin.

The term "aeration" as used herein refers to the dispersion of a gaseous material into a flowable fluid, for example to provide a diffusion surface to introduce a molecule or compound from the gas into the flowable surface. The term is not limited to the dispersion of air per se, although the use of air is preferred, but rather refers to the introduction of any gas to a flowable fluid, e.g. $O_2$, $CO_2$, hydrogen, nitrogen, and the like and mixtures thereof, The aeration of a fluid is preferably to allow molecules and/or compounds to diffuse to the fluid through the fluid-bubble interface following expulsion of the bubbles from the device of the invention into the surrounding fluid. A fluid may, however, also be aerated for aesthetic purposes, such as the addition of $CO_2$ to a beverage to provide carbonation.

DEVICE IN GENERAL

Different embodiments are shown and described herein (see FIGS. 1, 2 and 3) which could be used in producing the stable capillary microjet and/or a dispersion of particles which are substantially uniform in size. Although various embodiments are part of the invention, they are merely provided as exemplary devices which can be used to convey the essence of the invention, which is the formation of a stable capillary microjet and/or uniform dispersion of particles.

A basic device comprises (1) a means for supplying a first fluid, preferably a gas, and (2) a pressure chamber supplied with a second fluid which flows out of an exit opening in the pressure chamber, preferably a liquid. The exit opening of the pressure chamber is aligned with the flow path of the means for supplying the first fluid. The embodiments of FIGS. 1, 2 and 3 clearly show that there can be a variety of different means for supplying the first fluid.

Other means for supplying a first fluid flow stream will occur to those skilled in the art upon reading this disclosure.

Further, other configurations for forming the pressure chamber around the means for supplying the first fluid will occur to those skilled in the art upon reading this disclosure. Such other embodiments are intended to be encompassed by the present invention provided the basic conceptual results disclosed here are obtained, i.e. a stable capillary microjet is formed and/or a dispersion of particle highly uniform in size is formed. To simplify the description of the invention, the means for supplying a first fluid is often referred to as a cylindrical tube (see FIG. 1) and the first fluid is generally referred to as a gas. The gas can be any gas depending on the desired use of the device, although it is preferably air. For example, the gas could be air used to create small bubbles for aeration of a liquid to provide a gaseous medium through which components may diffuse into a liquid. Further, for purposes of simplicity, the second fluid is generally described herein as being a liquid, e.g. water. The invention is also generally described with a gas formulation being expelled from the supply means and forming a stable microjet due to interaction with surrounding water flow, which focuses the gas microjet to flow out of an exit of the pressure chamber.

Formation of the microjet and its acceleration and ultimate particle formation are based on the abrupt pressure drop associated with the steep acceleration experienced by the gas on passing through an exit orifice of the pressure chamber which holds the second fluid (i.e. the liquid). On leaving the chamber the flow undergoes a large pressure difference between the liquid and the gas, which in turn produces a highly curved zone on the liquid surface near the exit port of the pressure chamber and in the formation of a cuspidal point from which a steady microjet flows, provided the amount of the gas drawn through the exit port of the pressure chamber is replenished. Thus, in the same way that a glass lens or a lens of the eye focuses light to a given point, the flow of the liquid surrounds and focuses the gas into a stable microjet. The focusing effect of the surrounding flow of liquid creates a stream of gas which is substantially smaller in diameter than the diameter of the exit orifice of the pressure chamber. This allows the gas to flow out of the pressure chamber orifice without touching the orifice, providing advantages including the feature that the diameter of the stream and the resulting particles are smaller than the diameter of the exit orifice of the chamber. This is particularly desirable because it is difficult to precisely engineer holes which are very small in diameter. Further, in the absence of the focusing effect (and formation of a stable interface cusp) flow of gas out of an opening will result in particles which have a diameter greater than the diameter of the exit opening.

The description provided here generally indicates that the gas leaves the pressure chamber through an exit orifice surrounded by the liquid and thereafter enters into a liquid surrounding environment which may be either a hydrophobic or hydrophilic liquid. This configuration is particularly useful when it is necessary to create very small highly uniform bubbles which are moved into a liquid surrounding exit opening of the pressure chamber. The need for the formation of very small highly uniform bubbles into a gas occurs in a variety of different industrial applications. For example, water needs to be oxygenated in a variety of situations including small fish tanks for home use and large volume fisheries for industrial use. The additional oxygen can aid the rate of growth of the fish and thereby improve production for the fishery. In another embodiment, oxygen or air bubbles can be forced into liquid sewage in order to aid in treatment. In yet another application of the invention, contaminated gases such as a gas contaminated with a radioactive material can be formed into small uniformed bubbles and blown into a liquid, where the contamination in the gas will diffuse into the liquid, thereby cleaning the gas. The liquid will, of course, occupy substantially less volume and therefore be substantially easier to dispose of than contaminated toxic gas.

Those skilled in the art will recognize that variations on the different embodiments disclosed below will be useful in obtaining particularly preferred results. Specific embodiments of devices are now described.

EMBODIMENT OF FIG. 1

A first embodiment of the invention where the supply means is a cylindrical feeding needle supplying gas into a pressurized chamber of liquid: is described below with reference to FIG. 1.

Figure 1B:
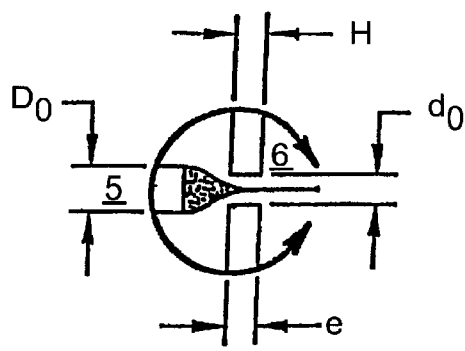

The components of the embodiment of FIG. 1 are as follows:
1. Feeding needle—also referred to generally as a fluid source and a tube.
2. End of the feeding needle used to insert the gas to be dispersed.
3. Pressure chamber.
4. Orifice used as liquid inlet.
5. End of the feeding needle used to evacuate the liquid to be atomized.
6. Orifice through which withdrawal takes place.
7. Atomize (spray)—also referred to as aerosol.

$D_0$=diameter of the feeding needle; $d_0$=diameter of the orifice through which the microjet is passed; e=axial length of the orifice through which withdrawal takes place; H=distance from the feeding needle to the microjet outlet; $P_0$ pressure inside the chamber; $P_\alpha$=atmospheric pressure.

Although the device can be configured in a variety of designs the different designs will all include the essential components shown in FIG. 1 or components which perform an equivalent function and obtain the desired results. Specifically, a device of the invention will be comprised of at least one source of a first fluid (e.g., a feeding needle with an opening 2) into which a first fluid such as a gas formulation can be fed and an exit opening 5 from which the gas can be expelled. The feeding needle 1, or at least its exit opening 5, is encompassed by a pressure chamber 3. The chamber 3 has inlet opening 4 which is used to feed a second fluid (e.g. a liquid) into the chamber 3 and an exit opening 6 through which liquid from the pressure chamber and gas from the feeding needle 3 are expelled. When the first fluid is a gas it is preferably expelled into a liquid to create bubbles.

In FIG. 1, the feeding needle and pressure chamber are configured to obtain a desired result of producing bubbles wherein the particles are small and uniform in size. The bubbles have a size which is in a range of 0.1 to 100 microns. The particles of any given bubbles will all have about the same diameter with a relative standard deviation of ±10% to ±30% or more preferably ±3% to ±10%. Stating that bubbles will have a diameter in a range of 1 to 5 microns does not mean that different bubbles will have different diameters and that some will have a diameter of 1 micron while others of 5 microns. The bubbles in a given dispersion will all (preferably about 90% or more) have the same diameter ±3% to ±30%. For example, the bubbles of a given dispersion will have a diameter of 2 microns ±3% to ±10%.

Such a uniform bubble monodispersion is created using the components and configuration as described above. However, other components and configurations will occur to those skilled in the art. The object of each design will be to supply fluid so that it creates a stable capillary microjet which is accelerated and stabilized by tangential viscous stress exerted by the second fluid on the first fluid surface. The stable microjet created by the second fluid leaves the pressurized area (e.g., leaves the pressure chamber and exits the pressure chamber orifice) and splits into particles or bubbles which have the desired size and uniformity.

The parameter window used (i.e. the set of special values for the properties of the liquid used, flow-rate used, feeding needle diameter, orifice diameter. pressure ratio. etc ) should be large enough to be compatible with virtually any liquid (dynamic viscosities in the range from $10^{-4}$ to 1 kg m$^{-1}$s$^{-1}$); in this way, the capillary microjet that emerges from the end of the feeding needle is absolutely stable and perturbations produced by breakage of the jet cannot travel upstream. Downstream, the microjet splits into evenly shaped bubbles simply by effeet of capillary instability (see, for example, Rayleigh, "On the instability of jets", Proc. London Math. Soc., 4–13, 1878), similar in a manner to a laminar capillary jet falling from a half-open tap.

When the stationary, steady interface is created, the capillary jet that emerges from the end of the drop at the outlet of the feeding point is concentrically withdrawn into the nozzle. After the jet emerges from the drop, the liquid is accelerated by tangential sweeping forces exerted by the gas stream flowing on its surface, which gradually decreases the jet cross-section. Stated differently the liquid flow acts as a lens and focuses and stabilizes the microjet as it moves toward and into the exit orifice of the pressure chamber. When the first fluid of the invention is a gas, and the second fluid is a liquid, the inertia of the first fluid is low, and the gas abruptly decelerates very soon after it issues from the cusp of the attached droplet. In such an instance, the microjet is so short that it is almost indistinguishable from the stable cusp of the gas-liquid interface.

The forces exerted by the second fluid flow on the first fluid surface should be steady enough to prevent irregular surface oscillations. Therefore, any turbulence in the gas motion should be avoided; even if the gas velocity is high, the characteristic size of the orifice should ensure that the gas motion is laminar (similar to the boundary layers formed on the jet and on the inner surface of the nozzle or hole).

STABLE CAPILLARY MICROJET

Figure 4:
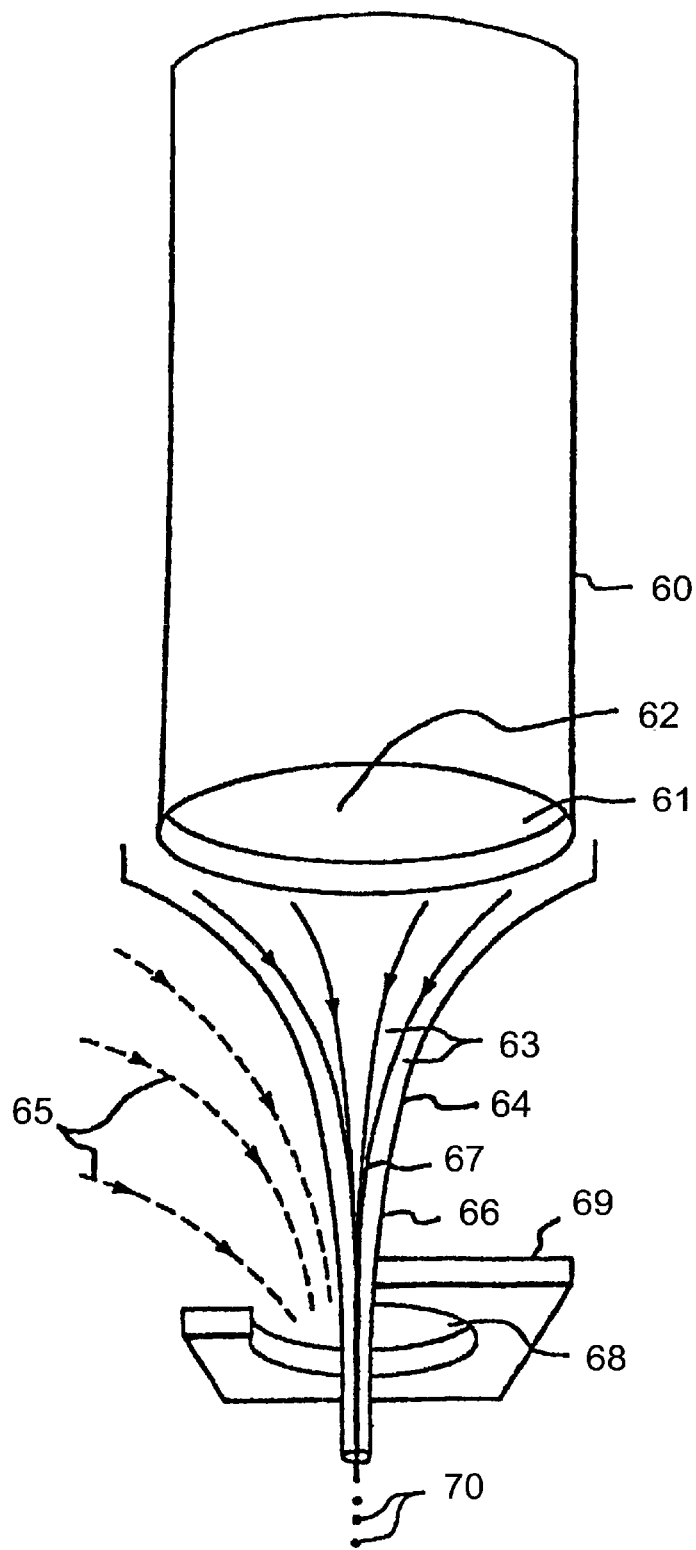
Figure 5:
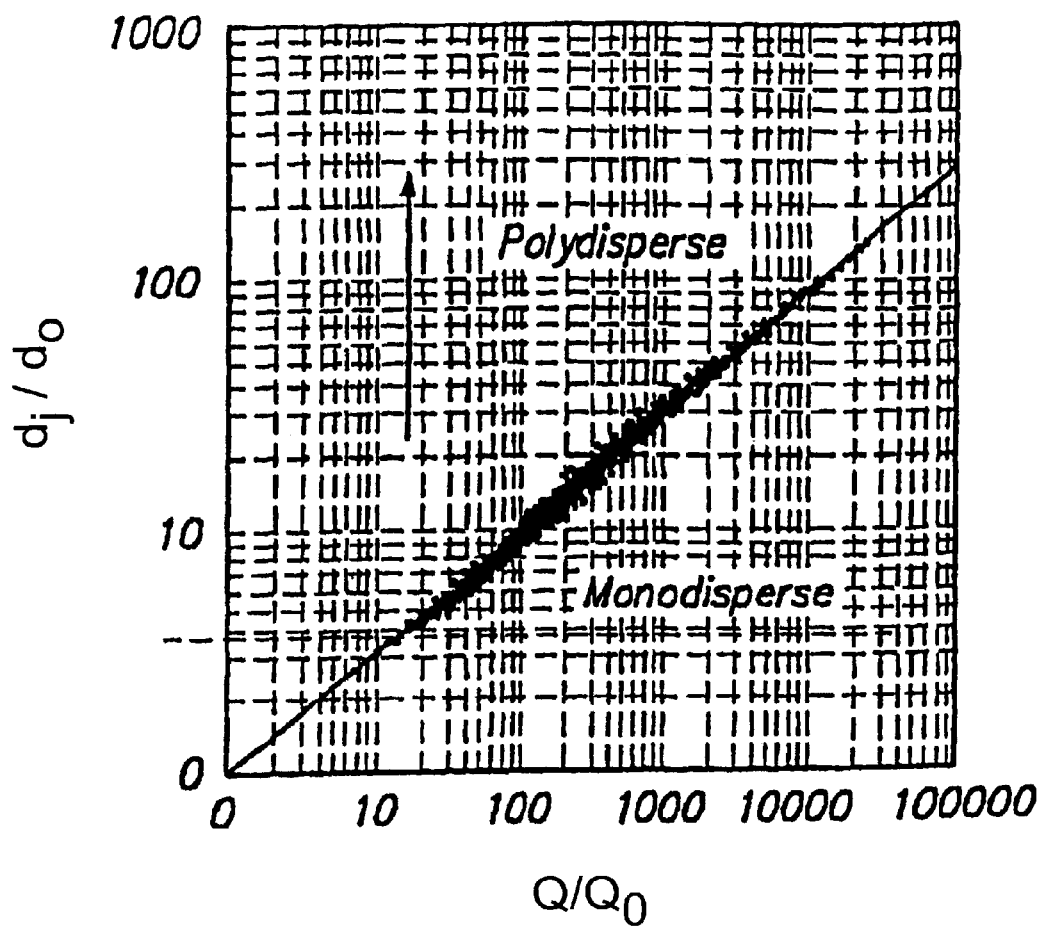
Figure 6:
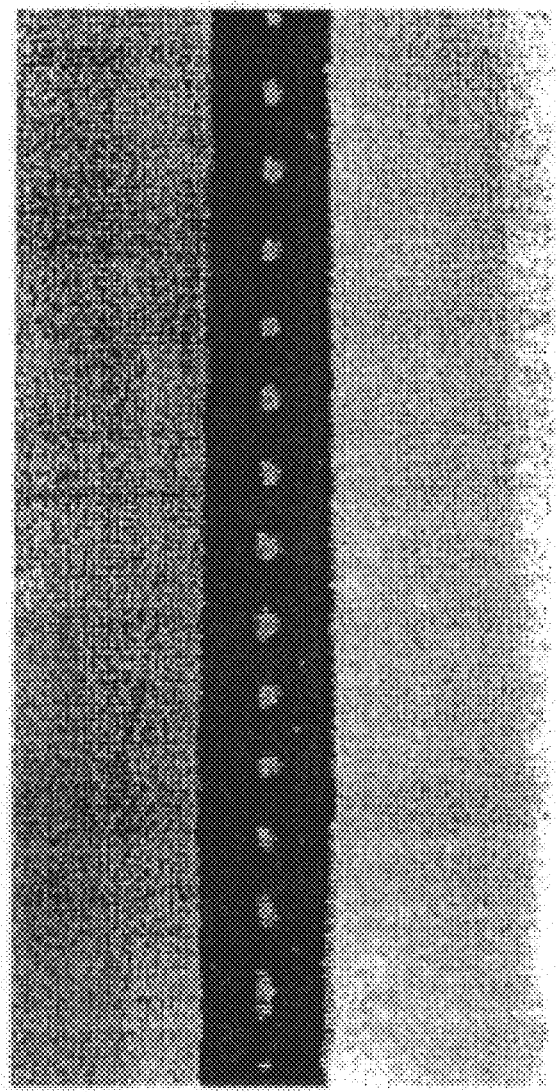

FIG. 4 illustrates the interaction of a gas and a liquid to form bubbles using the method of the invention. The feeding needle 60 has a circular exit opening 61 with an internal radius $R_0$ which feeds a gas 62 out of the end, forming a drop with a radius in the range of $R_0$ to $R_0$ plus the thickness of the wall of the needle. The exiting gas forms an infinite amount of streamlines 63 that interact with the surrounding liquid to form a stable cusp at the interface 64 of the two fluids. The surrounding liquid also forms an infinite number of liquid streamlines 65, which interact with the exiting gas to create a virtual focusing funnel 66. The exiting gas is focused by the focusing funnel 66 resulting in a stable capillary microjet 67, which remains stable until it exits the opening 68 of the pressure chamber 69. After exiting the pressure chamber, the microjet begins to break-up, forming monodispersed particles 70.

The liquid flow, which affects the gas withdrawal and its subsequent deceleration after the jet is formed, should be very rapid but also uniform in order to avoid perturbing the fragile capillary interface (the surface of the drop that emerges from the jet).

Gas flows out of the end of a capillary tube and forms a small gas drop at the end. The tube has an internal radius $R_o$. The drop has a radius in a range of from $R_o$ to $R_o$ plus the structural thickness of the tube as the drop exits the tube, and thereafter the drop narrows in circumference to a much smaller circumference as is shown in the expanded view of the tube (i.e. feeding needle) 5 as shown in FIGS. 1 and 4.

As illustrated in FIG. 4, the exit opening 61 of the capillary tube 60 is positioned close to an exit opening 68 in a planar surface of a pressure chamber 69. The exit opening 68 has a minimum diameter D and is in a planar member with a thickness L. The diameter D is referred to as a minimum diameter because the opening may have a conical configuration with the narrower end of the cone positioned closer to the source of liquid flow. Thus, the exit opening may be a funnel-shaped nozzle although other opening configurations are also possible, e.g. an hour glass configuration. Liquid in the pressure chamber continuously flows out of the exit opening. The flow of the liquid causes the gas drop expelled from the tube to decrease in circumference as the gas moves away from the end of the tube in a direction toward the exit opening of the pressure chamber.

In actual use, it can be understood that the opening shape which provokes maximum liquid acceleration (and consequently the most stable cusp and microjet with a given set of parameters) is a conically shaped opening in the pressure chamber. The conical opening is positioned with its narrower end toward the source of gas flow.

The distance between the end 61 of the tube 60 and the beginning of the exit opening 68 is H. At this point it is noted that $R_o$, D, H and L are all preferably on the order of hundreds of microns. For example, $R_o$=400 μm, D=150 μm, H=1 mm, L=300 μm. However, each could be 1/100 to 100× these sizes.

The end of the gas stream develops a cusp-like shape at a critical distance from the exit opening 68 in the pressure chamber 69 when the applied pressure drop $\Delta P_g$ across the exit opening 68 overcomes the liquid-gas surface tension stresses $\gamma/R^*$ appearing at the point of maximum curvature—e.g. $1/R^*$ from the exit opening.

A steady state is then established if the gas flow rate Q ejected from the drop cusp is steadily supplied from the capillary tube. This is the stable capillary cusp which is an essential characteristic of the invention needed to form the stable microjet. More particularly, a steady, thin gas jet with a typical diameter $d^j$ is smoothly emitted from the stable cusp-like drop shape and this thin gaseous jet extends over a distance in the range of microns to millimeters. The length of the stable microjet will vary from very short (e.g. 1 micron) to very long (e.g. 50 mm) with the length depending on the (1) flow-rate of the gas and (2) the Reynolds number of the gas stream flowing out of the exit opening of the pressure chamber. The gas jet is the stable capillary microjet obtained when supercritical flow is reached. As mentioned, in the case of a gas jet the microjet may be so small as to be almost indistinguishable from the stable cusp. This jet demonstrates a robust behavior provided that the pressure drop $\Delta P_1$ applied to the liquid is sufficiently large compared to the maximum surface tension stress (on the order of $\gamma/d_j$) that act at the liquid-gas interface. The jet has a slightly parabolic axial velocity profile which is, in large part, responsible for the stability of the microjet. The stable microjet is formed without the need for other forces, i.e. without adding force such as electrical forces on a charged fluid. However, for some applications it is preferable to add charge to particles, e.g. to cause the particles to adhere to a given surface. The shaping of liquid exiting the capillary tube by the gas flow forming a focusing funnel creates a cusp-like meniscus resulting in the stable microjet. This is a fundamental characteristic of the invention.

The microjet eventually destabilizes due to the effect of surface tension forces. Destabilization results from small natural perturbations moving downstream, with the fastest growing perturbations being those which govern the break up of the microjet, eventually creating a uniform sized monodispersion of bubbles 70 as shown in FIG. 4. The microjet, even as it initially destabilizes, passes out of the exit orifice of the pressure chamber without touching the peripheral surface of the exit opening.

MATHEMATICS OF A STABLE MICROJET

Cylindrical coordinates (r,z) are chosen for making a mathematical analysis of a stable microjet, i.e. fluid undergoing "supercritical flow." The cusp-like meniscus formed by the fluid coming out of the tube is pulled toward the exit of the pressure chamber by a pressure gradient created by the flow of a second, immiscible fluid.

The cusp-like meniscus formed at the tube's mouth is pulled towards the hole by the pressure gradient created by the liquid stream. From the cusp of this meniscus, a steady gas thread with the shape of radius r=ξ is withdrawn through the hole by the action of both the suction effect due to $\Delta_1$, and the tangential viscous stresses $\tau_s$ exerted by the liquid on the jet's surface in the axial direction. The averaged momentum equation for this configuration may be written:

$$\frac{d}{d_z}\left[P_g + \frac{\rho_g Q^2}{2\Pi^2 \xi^4}\right] = \frac{2\tau_s}{\xi}, \quad (1)$$

where Q is the gas flow rate upon exiting the feeding tube, $P_g$ is the gas pressure, and $\rho_g$ is the gas density, assuming that the viscous extensional term is negligible compared to the kinetic energy term, as will be subsequently justified. The gas pressure $P_g$ is given by the capillary equation.

$$P_g = P_1 + \gamma/\xi. \quad (2)$$

where $\gamma$ is the liquid-gas surface tension. As shown in the Examples, the pressure drop $\Delta P_1$ is sufficiently large as compared to the surface tension stress $\gamma/\xi$ to justify neglecting the latter in the analysis. This scenario holds for the whole range of flow rates in which the microjet is absolutely stable. In fact, it will be shown that, for a given pressure drop $\Delta P_1$, the minimum liquid flow rate that can be sprayed in steady jet conditions is achieved when the surface tension stress $\gamma/\xi$ is of the order of the kinetic energy of the liquid $\rho_1 Q^2/(2\pi^2\xi^4)$, since the surface tension acts like a "resistance" to the motion (it appears as a negative term in the right-hand side term of Eq. (1)). Thus, $$Q_{\min} \sim \left(\frac{\gamma d_j^3}{\rho_g}\right)^{1/2} \quad (3)$$

For sufficiently large flow rates Q compared to $Q_{min}$, the simplified averaged momentum equation in the axial direction can be expressed as $$\frac{d}{d_z}\left(\frac{\rho_g Q^2}{2\Pi^2\xi^4}\right) = \frac{dP_1}{d_z} + \frac{2\tau_s}{\xi}, \quad (4)$$

where one can identify the two driving forces for the gas flow on the right-hand side. This equation can be integrated provided the following simplification is made: if one uses a thin plate with thickness L of the order or smaller than the hole's diameter D (which minimizes downstream perturbations in the liquid flow), the pressure gradient up to the hole exit is on the average much larger than the viscous shear term $2\tau_s/\xi$ owning to the surface stress. On the other hand, the axial viscous term is of the order $O[\mu^2 Q/D^2 d_j^2]$, since the hole diameter D is actually the characteristic distance associated with the gas flow at the hole's entrance in both the radial and axial directions. This term is very small compared to the pressure gradient in real situations, provided that $\Delta P_1 >> \mu^2/D^2\rho_g$ (which holds, e.g., for liquids with viscosities as large as 100 cpoises, using hole diameters and pressure drops as small as $D \sim 10\ \mu m$ and $\Delta P_g \geqq 100$ mbar). The neglect of all viscous terms in Eq. (4) is then justified. Notice that in this limit on the liquid flow is quasi-isentropic in the average (the liquid almost follows Bernoulli equation) as opposed to most micrometric extensional flows. Thus, integrating (4) from the stagnation regions of both fluids up to the exit, one obtains a simple and universal expression for the jet diameter at the hole exit:

$$d_j \simeq \left(\frac{8\rho_g}{\Pi^2 \Delta P_l}\right)^{1/4} Q^{1/2}, \quad (5)$$

which for a given pressure drop $\Delta P_1$ is independent of geometrical parameters (hole and tube diameters. tube-hole distance, etc.), liquid and gas viscosities, and liquid-gas surface tension.

This diameter remains almost constant up to the breakup point since the gas pressure after the exit remains constant.

MONODISPERSE PARTICLES

Above the stable microjet undergoing "supercritical flow" is described and it can be seen how this aspect of the invention can be made use of in a variety of industrial applications. When the microjet exits the pressure chamber the gas pressure $P_g$ becomes (like the liquid pressure $P_1$) almost constant in the axial direction, and the jet diameter remains almost constant up to the point where it breaks up by capillary instability. Defining a Weber number $We = (\rho_1 v_1^2 d_j)/\gamma \sim 2\Delta P_1 d_j/\gamma$ (where $v_1$ is the liquid velocity measured at the orifice), below a certain experimental value $We_c \sim 40$ the breakup mode is axisymnetric and the resulting droplet stream is characterized by its monodispersity provided that the fluctuations of the gas flow do not contribute to droplet coalescence (these fluctuations occur when the gas stream reaches a fully developed turbulent profile around the liquid jet breakup region). Above this $We_c$ value, sinuous nonaxisymmetric disturbances, coupled to the axisymmetric ones, become apparent. For larger We numbers, the nonlinear growth rate of the sinuous disturbances seems to overcome that of the axisymmetric disturbances. The resulting spray shows significant polydispersity in this case. Thus, it can be seen that by controlling parameters to keep the resulting Weber number to 40 or less, allows the bubbles formed to be all substantially the same size. The size variation is about ±3% to ±30% and move preferably ±3% to ±10%. These particles can have a desired size e.g. 0.1 microns to 50 microns.

The shed vorticity influences the breakup of the jet and thus the formation of the particles. Upstream from the hole exit, in the accelerating region, the gas stream is laminar. Typical values of the Reynolds number range from 500 to 6000 if a velocity of the order of the speed of sound is taken as characteristic of the velocity of the liquid. Downstream from the hole exit, the cylindrical mixing layer between the gas stream and the stagnant gas becomes unstable by the classical Kelvin-Helmholtz instability. The growth rate of the thickness of this layer depends on the Reynolds number of the flow and ring vortices are formed at a frequency of the order of $v_1/D$, where D is the hole diameter. Typical values of $v_1$ and D as those found in our experimental technique lead to frequencies or the order of MHZ which are comparable to the frequency of drop production (of order of $t_b^{-1}$).

Given the gas flow rate and the hole diameter, a resonance frequency which depends on the gas velocity (or pressure difference driving the gas stream) can be adjusted (tuned) in such a way that vortices act as a forcing system to excite perturbations of a determined wavelength on the jet surface. Experimental results obtained clearly illustrates the different degree of coupling between the two gas-liquid coaxial jets. In one set of experimental results the bubble sizes are shown to have a bubble size of about 5.7 microns with a standard deviation of 12%. This results when the velocity of the liquid has been properly tuned to minimize the dispersion in the size of droplets resulting from the jet breakup. In this case, the flow rate of the gas jet and its diameter are 0.08 $\mu l\ s^{-1}$ and 3 $\mu m$, respectively. Data have been collected using a MASTERSIZER from MALVERN Instruments. As the degree of coupling decreases, perturbations at the jet surface of different wavelengths become excited and, as it can be observed from the size distributions, the dispersion of the spray increases.

The liquid flow should be laminar in order to avoid a turbulent regime—turbulent fluctuations in the gas flow which have a high frequency and would perturb the liquid-gas interface. The Reynolds numbers reached at the orifice are $$Re = \frac{v_l d_0}{v_l} \sim 4000$$

where $v_1$ is the kinematic viscosity of the liquid. Even though this number is quite high, there are large pressure gradients downstream (a highly convergent geometry), so that a turbulent regime is very unlikely to develop.

The essential difference from existing pneumatic atomizers (which possess large Weber numbers) and the present invention is that the aim of the present invention is not to rupture the liquid-gas interface but the opposite, i.e. to increase the stability of the interface until a capillary jet is obtained. The jet, which will be very thin provided the pressure drop resulting from withdrawal is high enough, splits into drops the sizes of which are much more uniform than those resulting from disorderly breakage of the liquid-gas interface in existing pneumatic atomizers.

The proposed system obviously requires delivery of the gas to be atomized and the liquid to be used in the resulting drop production. Both should be fed at a rate ensuring that the system lies within the stable parameter window. Multiplexing is effective when the flow-rates needed exceed those on an individual cell. More specifically, a plurality of feeding sources or feeding needles may be used to increase the rate at which aerosols are created. The flow-rates used should also ensure the mass ratio between the flows is compatible with the specifications of each application.

The gas and liquid can be dispensed by any type of continuous delivery system (e.g. a compressor or a pressurized tank the former and a volumetric pump or a pressurized bottle the latter). If multiplexing is needed, the liquid flow-rate should be as uniform as possible among cells; this may entail propulsion through several capillary needles, porous media or any other medium capable of distributing a uniform flow among different feeding points.

Each individual device should consist of a feeding point (a capillary needle, a point with an open microchannel, a microprotuberance on a continuous edge, etc.) 0.002–2 mm (but, preferentially 0.01–0.4 mm) in diameter, where the drop emerging from the microjet can be anchored, and a small orifice 0.002–2 mm (preferentially 0.01–0.25 mm) in diameter facing the drop and separated 0.01–2 mm (preferentially 0.2–0.5 mm) from the feeding point. The orifice communicates the withdrawal liquid around the drop, at an increased pressure, with the zone where the atomizate is produced, at a decreased pressure. The device can be made from a variety of materials (metal, polymers, ceramics, glass).

FIG. 1 depicts a tested prototype where the gas to be atomized is inserted through one end of the system 2 and the liquid in introduced via the special inlet 4 in the pressure chamber 3. The prototype was tested at gas feeding rates from 100 to 2000 mBar above the atmospheric pressure $P_\alpha$ at which the atomized gas was discharged. The whole enclosure around the feeding needle 1 was at a pressure $P_0 > P_\alpha$. The gas feeding pressure, $P_1$, should always be slightly higher than the gas propelling pressure, $P_o$. Depending on the pressure drop in the needle and the gas feeding system, the pressure difference ($P_1 = P_0 > 0$) and the flow-rate of the gas to be atomized, Q are linearly related provided the flow is laminar—which is indeed the case with this prototype. The critical dimensions are the distance from the needle to the plate (H), the needle diameter ($D_0$), the diameter of the orifice through which the microjet 6 is discharged ($d_0$) and the axial length, e, of the orifice (i.e. the thickness of the plate where the orifice is made). In this prototype, H was varied from 0.3 to 0.7 mm on constancy of the distances ($D_0$=0.45 mm, $d_0$–0.2 mm) and e–0.5 mm. The quality of the resulting spray 7 did not vary appreciably with changes in H provided the operating regime (i.e. stationary drop and microjet) was maintained. However, the system stability suffered at the longer H distances (about 0.7 mm). The other atomizer dimensions had no effect on the spray or the prototype functioning provided the zone around the needle (its diameter) was large enough relative to the feeding needle.

WEBER NUMBER

Adjusting parameters to obtain a stable capillary microjet and control its breakup into monodisperse particle is governed by the Weber number and the liquid-to-gas velocity ratio or α which equal $V_1/V_g$. The Weber number or "We" is defined by the following equation:

$$We = \frac{\rho_l V_l^2 d}{\gamma}$$

wherein $\rho_1$ is the density of the gas, d is the diameter of the stable microjet, γ is the liquid-gas surface tension, and $V_1^2$ is the velocity of the gas squared.

When carrying out the invention the parameters should be adjusted so that the Weber number is greater than 1 in order to produce a stable capillary microjet. However, to obtain a particle dispersion which is monodisperse (i.e. each particle has the same size ±3 to ±30%) the parameters should be adjusted so that the Weber number is less than 40. The monodisperse aerosol is obtained with a Weber number in a range of about 1 to about 40 when the breaking time is sufficiently small to avoid non-symmetric perturbations. ($1 \leqq We \leqq 40$)

OHNESORGE NUMBER

A measure of the relative importance of viscosity on the jet breakup can be estimated from the Ohnesorge number defined as the ratio between two characteristic times: the viscous time $t_\nu$ and the breaking time $t_b$. The breaking time $t_b$ is given by [see Rayleigh (1878)]

$$t_b \sim \left(\frac{\rho_g d^2}{\gamma}\right)^{1/2}. \tag{2}$$

Perturbations on the jet surface are propagated inside by viscous diffusion in times $t_\nu$ of the order of $$t_{\nu \sim \rho g} d^{2/\mu}{}_g, \tag{3}$$

where $\mu_1$ is the viscosity of the liquid. Then, the Ohnesorge number, Oh, results $$Oh = \frac{\mu_g}{(\rho_g \gamma d)^{1/2}}. \tag{4}$$

If this ratio is much smaller than unity viscosity plays no essential role in the phenomenon under consideration. Since the maximum value of the Ohnesorge number in actual experiments conducted is as low as $3.7 \times 10^{-2}$, viscosity plays no essential role during the process of jet breakup.

EMBODIMENT OF FIG. 2

A variety of configurations of components and types of fluids will become apparent to those skilled in the art upon reading this disclosure. These configurations and fluids are encompassed by the present invention provided they can produce a stable capillary microjet of a first fluid from a source to an exit port of a pressure chamber containing a second fluid. The stable microjet is formed by the first fluid flowing from the feeding source to the exit port of the pressure chamber being accelerated and stabilized by tangential viscous stress exerted by the second fluid in the pressure chamber on the surface of the first fluid forming the microjet. The second fluid forms a focusing funnel when a variety of parameters are correctly tuned or adjusted. For example, the speed, pressure, viscosity and miscibility of the first and second fluids are chosen to obtain the desired results of a stable microjet of the first fluid focused into the center of a funnel formed with the second fluid. These results are also obtained by adjusting or tuning physical parameters of the device, including the size of the opening from which the first fluid flows, the size of the opening from which both fluids exit, and the distance between these two openings.

The embodiment of FIG. 1 can, itself, be arranged in a variety of configurations. Further, as indicated above, the embodiment may include a plurality of feeding needles. A plurality of feeding needles may be configured concentrically in a single construct, as shown in FIG. 2.

Figure 2:
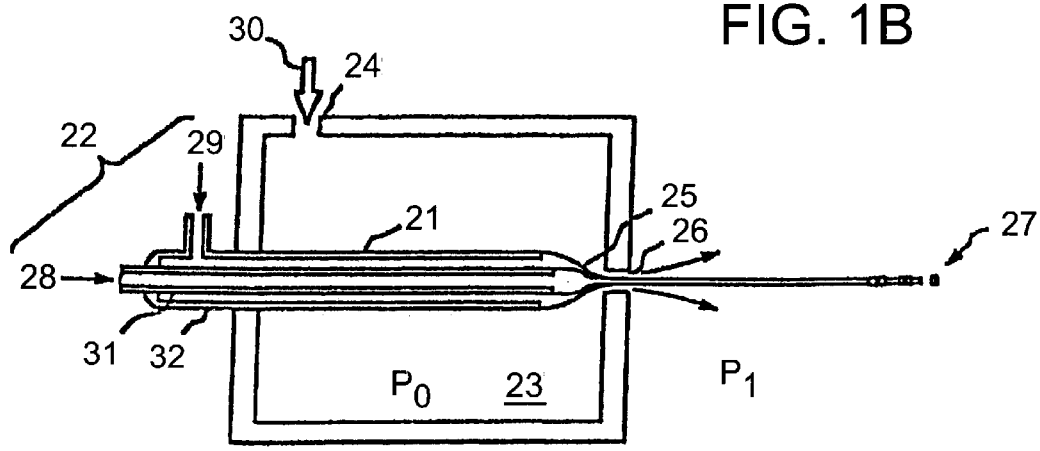
Figure 3B:
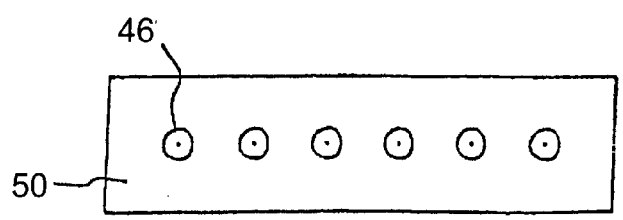
Figure 3A:
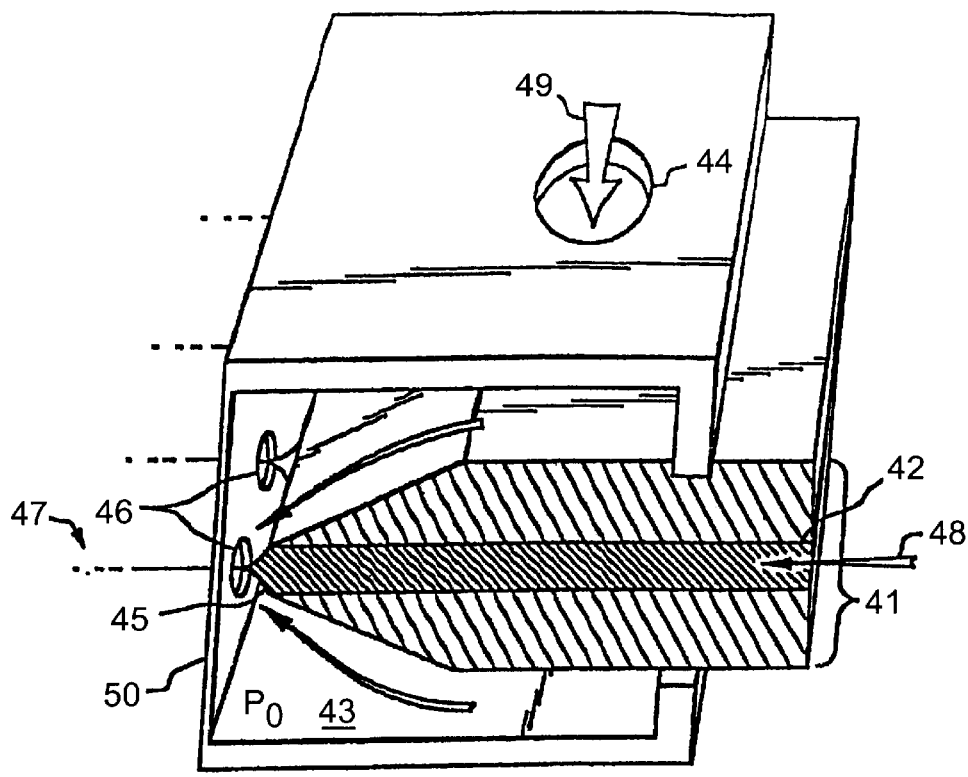
Figure 3C:
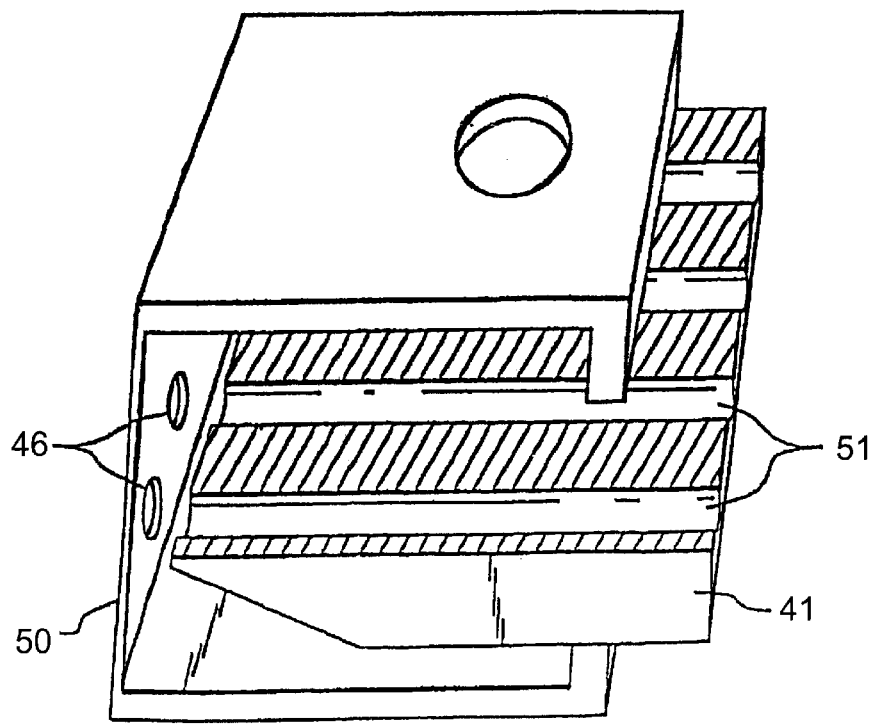

The components of the embodiment of FIG. 2 are as follows:

21. Feeding needle—tube or source of fluid.
22. End of the feeding needle used to insert the liquids to be atomized.
23. Pressure chamber.
24. Orifice used as liquid inlet.
25. End of the feeding needle used to evacuate the gas to be atomized.
26. Orifice through which withdrawal takes place.
27. Atomizate (spray) or aerosol.
28. First gas to be atomized (inner core of particle).
29. Second fluid to be atomized (outer coating of particle).
30. Liquid for creation of microjet.
31. Internal tube of feeding needle.
32. External tube of feeding needle.

D=diameter of the feeding needle; d=diameter of the orifice through which the microjet is passed; e=axial length of the orifice through which withdrawal takes place; H=distance from the feeding needle to the microjet outlet; $\gamma$=surface tension; $P_0$=pressure inside the chamber; $P_\alpha$=atmospheric pressure.

The embodiment of FIG. 2 is preferably used when attempting to form a spherical particle of one substance surrounded by another substance. The device of FIG. 2 is comprised of the same basic component as per the device of FIG. 1 and further includes a second feeding source 32 which is positioned concentrically around the first cylindrical feeding source 31. The second feeding source may be surrounded by one or more additional feeding sources with each concentrically positioned around the preceding source.

The process is based on the microsuction which the liquid-gas or liquid-liquid interphase undergoes (if both are immiscible), when said interphase approaches a point beginning from which one of the fluids is suctioned off while the combined suction of the two fluids is produced. The interaction causes the fluid physically surrounded by the other to form a capillary microjet which finally breaks into spherical drops. If instead of two fluids (gas-liquid), three or more are used that flow in a concentric manner by injection using concentric tubes, a capillary jet composed of two or more layers of different fluids is formed which, when it breaks, gives rise to the formation of spheres composed of several approximately concentric spherical layers of different fluids. The size of the outer sphere (its thickness) and the size of the inner sphere (its volume) can be precisely adjusted. This can allow the manufacture of layered bubbles for a variety of end uses.

The method is based on the breaking of a capillary microjet composed of a nucleus of a gas and surrounded by other liquids and gases which are in a concentric manner injected by a special injection head, in such a way that they form a stable capillary microjet and that they do not mix by diffusion during the time between when the microjet is formed and when it is broken. When the capillary microjet is broken into spherical drops under the proper operating conditions, which will be described in detail below, these drops exhibit a spherical nucleus, the size and eccentricity of which can be controlled.

In the case of spheres containing two materials, the injection head 25 consists of two concentric tubes with an external diameter on the order of one millimeter. Through the internal tube 31 is injected the material that will constitute the nucleus of the microsphere, while between the internal tube 31 and the external tube 32 the coating is injected. The fluid of the external tube 32 joins with the fluid of tube 31 as the fluids exit the feeding needle, and the fluids thus injected are accelerated by a stream of gas or liquid that passes through a small orifice 26 facing the end of the injection tubes. When the drop in pressure across the orifice 26 is sufficient, the fluids form a completely stationary capillary microjet, if the quantities of liquids that are injected are stationary. This microjet does not touch the walls of the orifice, but passes through it wrapped in the stream of gas or funnel formed by gas from the tube 32. Because the funnel of fluid focuses the exiting fluid, the size of the exit orifice 26 does not dictate the size of the particles formed.

When the parameters are correctly adjusted, the movement of the fluid is uniform at the exit of the orifice 26 and the viscosity forces are sufficiently small so as not to alter either the flow or the properties of the liquids; for example, if there are biochemical molecular specimens having a certain complexity and fragility, the viscous forces that would appear in association with the flow through a micro-orifice might degrade these substances.

FIG. 2 shows a simplified diagram of the feeding needle 21, which is comprised of the concentric tubes 31, 32 through the internal and external flows of the fluids 28, 29 that are going to compose the microspheres comprised of two immiscible fluids. The difference in pressures $P_0-P_\alpha$ ($P_0>P_\alpha$) through the orifice 26 establishes a flow of liquid present in the chamber 23 and which is going to surround the microjet at its exit. The same pressure gradient that moves the liquid is the one that moves the microjet in an axial direction through the hole 26, provided that the difference in pressures $P_0-P_\alpha$ is sufficiently great in comparison with the forces of surface tension, which create an adverse gradient in the direction of the movement.

There are two limitations for the minimum sizes of the inside and outside jets that are dependent (a) on the surface tensions γ1 of the outside fluid 29 with the liquid 30 and γ2 of the outside fluid 29 with the inside fluid (e.g. gas) 28, and (b) on the difference in pressures $\Delta P = P_{0-P\alpha}$ through the orifice 26. In the first place, the jump in pressures $\Delta P$ must be sufficiently great so that the adverse effects of the surface tension are minimized. This, however, is attained for very modest pressure increases: for example, for a 10 micron jet of a gas having a surface tension of 0.05 N/m (tap water), the necessary minimum jump in pressure is in the order of 0.05 (N/m)/0.00001 m=$\Delta P$=50 mBar. But, in addition, the breakage of the microjet must be regular and axilsymmetric, so that the drops will have a uniform size, while the extra pressure $\Delta P$ cannot be greater than a certain value that is dependent on the surface tension of the outside gas with the gas γ1 and on the outside diameter of the microjet. It has been experimentally shown that this difference in pressures cannot be greater than 20 times the surface tension γ1 divided by the outside radius of the microjet.

Therefore, given some inside and outside diameters of the microjet, there is a range of operating pressures between a minimum and a maximum; nonetheless, experimentally the best results are obtained for pressures in the order of two to three times the minimum.

The viscosity values of the gases must be such that the gases with the greater viscosity $\mu_{max}$ verifies, for a diameter d of the jet predicted for this gas and a difference through the orifice $\Delta P$, the inequality:

$$\mu_{max} \leq \frac{\Delta P d^2 D}{Q}$$

With this, the pressure gradients can overcome the extensional forces of viscous resistance exerted by the gas when it is suctioned toward the orifice.

Moreover, the gases must have very similar densities in order to achieve the concentricity of the nucleus of the microsphere, since the relation of velocities between the gases moves according to the square root of the densities v1/v2=$(\rho 2/\rho 1)^{1/2}$ and both jets, the inside jet and the outside jet, must assume the most symmetrical configuration possible, which does not occur if the fluids have different velocities (FIG. 2). Nonetheless, it has been experimentally demonstrated that, on account of the surface tension γ2 between the two fluids, the nucleus tends to migrate toward the center of the microsphere, within prescribed parameters.

The distance between the plane of the internal tube 31 (the one that will normally project more) and the plane of the orifice may vary between zero and three outside diameters of the external tube 32, depending on the surface tensions between the fluids and with the liquid, and on their viscosity values. Typically, the optimal distance is found experimentally for each particular configuration and each set of liquids used.

The proposed dispersion system obviously requires fluids that are going to be used in the resulting bubbles to have certain flow parameters. Accordingly, flows for this use must be:

Flows that are suitable so that the system falls within the parametric window of stability. Multiplexing (i.e. several sets of concentric tubes) may be used, if the flows required are greater than those of an individual cell.

Flows that are suitable so that the mass relation of the fluids falls within the specifications of each application. Of course, a greater flow of liquid may be supplied externally by any means in specific applications, since this does not interfere with the functioning of the atomizer.

If the flows are varied, the characteristic time of this variation must be less than the hydrodynamic residence times of liquid and gas in the microjet, and less than the inverse of the first natural oscillation frequency of the drop formed at the end of the injection needle.

Therefore, any means for continuous supply of gas (compressors, pressure deposits, etc.) and of liquid (volumetric pumps, pressure bottles, etc.) may be used. If multiplexing is desired, the flow of gas must be as homogeneous as possible between the various cells, which may require impulse through multiple capillary needles, porous media, or any other medium capable of distributing a homogeneous flow among different feeding points.

Each dispersion device will consist of concentric tubes 31, 32 with a diameter ranging between 0.05 and 2 mm, preferably between 0.1 and 0.4 mm, on which the drop from which the microjet emanates can be anchored, and a small orifice (between 0.001 and 2 mm in diameter, preferably between 0.1 and 0.25 mm), facing the drop and separated from the point of feeding by a distance between 0.001 and 2 mm, preferably between 0.2 and 0.5 mm. The orifice puts the liquid that surrounds the drop, at higher pressure, in touch with the area in which the dispersion is to be attained, at lower pressure.

EMBODIMENT OF FIG. 3

The embodiments of FIGS. 1 and 2 are similar in a number of ways. Both have a feeding piece which is preferably in the form of a feeding needle with a circular exit opening. Further, both have an exit port in the pressure chamber which is positioned directly in front of the flow path of fluid out of the feeding source. Precisely maintaining the alignment of the flow path of the feeding source with the exit port of the pressure chamber can present an engineering challenge particularly when the device includes a number of feeding needles. The embodiment of FIG. 3 is designed to simplify the manner in which components are aligned. The embodiment of FIG. 3 uses a planar feeding piece (which by virtue of the withdrawal effect produced by the pressure difference across a small opening through which fluid is passed) to obtain multiple microjets which are expelled through multiple exit ports of a pressure chamber thereby obtaining multiple dispersionl streams. Although a single planar feeding member as shown in FIG. 3 it, of course, is possible to produce a device with a plurality of planar feeding members where each planar feeding member feeds fluid to a linear array of outlet orifices in the surrounding pressure chamber. In addition, the feeding member need not be strictly planar, and may be a curved feeding device comprised of two surfaces that maintain approximately the same spatial distance between the two pieces of the feeding source. Such curved devices may have any level of curvature, e.g. circular, semicircular, elliptical, hemi-elliptical, etc.

The components of the embodiment of FIG. 3 are as follows:

41. Feeding piece.

42. End of the feeding piece used to insert the gas to be dispersed.

43. Pressure chamber.

44. Orifice used as liquid inlet.

45. End of the feeding needle used to evacuate the gas to be dispersed.

46. Orifices through which withdrawal takes place.

47. Dispersion bubbles.

48. First fluid containing material to be dispersed.

49. Second fluid for creation of microjet.

50. Wall of the propulsion chamber facing the edge of the feeding piece.

51. Channels for guidance of fluid through feeding piece.

$d_j$=diameter of the microjet formed; $\rho_A$=density of first fluid (48); $\rho_B$=density of second fluid (49); $v_A$=velocity of the first fluid (48); $v_B$=velocity of the second fluid (49); e=axial length of the orifice through which withdrawal takes place; H =distance from the feeding needle to the microjet outlet; $P_0$=pressure inside the chamber; $\Delta P_g$=change in pressure of the gas; $P_\alpha$=atmospheric pressure; Q=volumetric flow rate The proposed dispersion device consists of a feeding piece 41 which creates a planar feeding channel through which a where a first fluid 48 flows. The flow is preferably directed through one or more channels of uniform bores that are constructed on the planar surface of the feeding piece 41. A pressure chamber 43 that holds the propelling flow of a second liquid 49, houses the feeding piece 41 and is under a pressure above maintained outside the chamber wall 50. One or more orifices, openings or slots (outlets) 46 made in the wall 52 of the propulsion chamber face the edge of the feeding piece. Preferably, each bore or channel of the feeding piece 41 has its flow path substantially aligned with an outlet 46.

When the second fluid 49 is a liquid and the first fluid 48 is a gas, the facts that the liquid is much more viscous and that the gas is much less dense virtually equalize the fluid and gas velocities. The gas microthread formed is much shorter; however, because its rupture zone is almost invariably located in a laminar flowing stream, dispersion in the size of the microbubbles formed is almost always small. At a volumetric gas flow-rate $Q_g$ and a liquid overpressure $\Delta P_1$, the diameter of the gas microjet is given by $$d_j \cong \left(\frac{8\rho_l}{\pi^2 \Delta P_l}\right)^{1/4} Q_g^{1/2}$$

The low liquid velocity and the absence of relative velocities between the liquid and gas lead to the Rayleigh relation between the diameters of the microthread and those of the bubbles (i.e. d =1.89$d_j$).

OXYGENATION OF WATER

More fish die from a lack of oxygen than any other cause. Fish exposed to low oxygen conditions become much more vulnerable to disease, parasites and infection, since low oxygen levels will (1) lower the oxidation/reduction potential (ORP) (2) favor growth of disease causing pathogens and (3) disrupt the function of many commercially available biofilters. Moreover, stress will reduce the fish activity level, growth rate, and may interfere with proper development. A continuous healthy minimum of oxygen is approximately a 6 parts per million (ppm) oxygen:water ratio, which is approximately 24 grams of dissolved oxygen per 1000 gallons of water. Fish consume on average 18 grams of oxygen per hour for every ten pounds of fish. Low level stress and poor feeding response can be seen at oxygen levels of 4–5 ppm. Acute stress, no feeding and inactivity can be seen at oxygen levels of 2–4 ppm, and oxygen levels of approximately 1–2 ppm generally result in death. These numbers are merely a guideline since a number of variable (e.g., water temperature, water quality, condition of fish, level of other gasses, etc.) all may impact on actual oxygen needs.

Proper aeration depends primarily on two factors: the gentleness and direction of water flow and the size and amount of the air bubbles. With respect to the latter, smaller air bubbles are preferable because they (1) increase the surface are between the air and the water, providing a larger area for oxygen diffusion and (2) smaller bubbles stay suspended in water longer, providing a greater time period over which the oxygen may diffuse into the water.

The technology of the invention provides a method for aerating water for the proper growth and maintenance of fish. A device of the invention for such a use would provide an oxygenated gas, preferably air, as the first fluid, and a liquid, preferably water, as the second fluid. The air provided in a feeding source will be focused by the flow of the surrounding water, creating a stable cusp at the interface of the two fluids. The particles containing the gas nucleus, and preferably air nucleus, are expelled into the liquid medium where aeration is desired.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A monodispersion of bubbles for aeration of a liquid, comprising at least about one thousand bubbles, wherein the bubbles have a diameter in a range of from about 0.1 micron to about 100 microns and wherein the dispersion is characterized by substantially all the bubbles having approximately the same diameter with a deviation in diameter of about ±3%.

2. The monodispersion of claim 1, wherein the bubbles are comprised of a gas selected from the group consisting of air, oxygen, and carbon dioxide, and wherein the liquid is aqueous.

3. The monodispersion of claim 1, wherein the gas is contaminated with a compound soluble in the liquid.

4. The monodispersion of claim 2, wherein the aqueous liquid is selected from the group consisting of water, sweetened water, and sewage.

5. The monodispersion of claim 1, wherein the bubbles are created by a flow stream of gas from a source through a second liquid in a pressure chamber, and wherein the second liquid is forced out of an exit orifice of the pressure chamber while surrounding and focusing the flow stream of gas into the first liquid where the focused flow stream of gas breaks up to form the bubbles.

6. The monodispersion as set forth in claim 1, formed by the process comprising:

forcing a gas from a source opening into a first liquid in a manner so as to create a flow stream of the gas through the first liquid, wherein the gas is comprised of molecules to be diffused into a second liquid;

moving the first liquid in a pressure chamber surrounding the source opening, out of an exit orifice in the pressure chamber wherein the flow stream of the gas flows out the exit orifice into the second liquid wherein the flow stream breaks up forming bubbles of the gas in the second liquid.

7. The monodispersion of claim 6, wherein the molecules in the gas diffuse into the second liquid.

8. The monodispersion of claim 6, wherein the bubbles are emitted at regularly spaced intervals from the exit orifice of the pressure chamber.

9. The method of claim 6, wherein the liquid is liquid sewage.

10. The method of claim 6, wherein the gas is carbon dioxide and the second liquid is aqueous.

11. A monodispersion of bubbles for aeration of a liquid, comprising at least about one thousand bubbles, wherein the bubbles have a diameter in a range of form about 0.1 micron to about 100 microns and wherein the dispersion is characterized by substantially all the bubbles having approximately the same diameter with a deviation in diameter of about ±3%, wherein said monodispersion is formed by a process comprising the following steps:

forcing a gas from a source opening into a first liquid in a manner so as to create a flow stream of the gas through the first liquid, wherein the gas is comprised of molecules to be diffused into a second liquid;

moving the first liquid in a pressure chamber surrounding the source opening, out of an exit orifice in the pressure chamber wherein the flow stream of the gas flows out the exit orifice into the second liquid wherein the flow stream breaks up forming bubbles of the gas in the second liquid.

12. The monodispersion of claim 11, wherein the bubbles are comprised of a gas selected from the group consisting of air, oxygen, and carbon dioxide, and wherein the liquid is aqueous.

13. The monodispersion of claim 11, wherein the gas is contaminated with a compound soluble in the liquid.

14. The monodispersion of claim 12, wherein the aqueous liquid is selected from the group consisting of water, sweetened water, and sewage.

15. The monodispersion of claim 11, wherein the bubbles are emitted at regularly spaced intervals from the exit orifice of the pressure chamber.

16. A mixture comprising diffused components, wherein said components are diffused into the mixture by a process comprising the following steps:

forcing a gas from a source opening into a first liquid in a manner so as to create a flow stream of the gas through the first liquid, wherein the gas is comprised of molecules to be diffused into a second liquid;

moving the first liquid in a pressure chamber surrounding the source opening, out of an exit orifice in the pressure chamber wherein the flow stream of the gas flows out the exit orifice into the second liquid wherein the flow stream breaks up forming bubbles of the gas in the second liquid, and wherein said second liquid and said bubbles of gas form a mixture of diffused components and further wherein the bubbles are emitted at regularly spaced intervals from the exit orifice of the pressure chamber and substantially all the bubbles have approximately the same diameter with a deviation in diameter of about ±3%.

17. The mixture of claim 16, wherein the bubbles are comprised of a gas selected from the group consisting of air, oxygen, and carbon dioxide, and wherein the liquid is aqueous.

18. The mixture of claim 16, wherein the gas is contaminated with a compound soluble in the liquid.

19. The mixture of claim 16, wherein the aqueous liquid is selected from the group consisting of water, sweetened water, and sewage.

20. A liquid comprising a monodispersion of bubbles, wherein said monodispersion comprises at least about one thousand bubbles, wherein the bubbles have a diameter in a range of form about 0.1 micron to about 100 microns and wherein substantially all the bubbles have approximately the same diameter with a deviation in diameter wherein the bubbles are diffused into a liquid by a process comprising the following steps:

forcing a gas from a source opening into a first liquid in a manner so as to create a flow stream of the gas through the first liquid, wherein the gas is comprised of molecules to be diffused into a second liquid;

moving the first liquid in a pressure chamber surrounding the source opening, out of an exit orifice in the pressure chamber wherein the flow stream of the gas flows out the exit orifice into the second liquid wherein the flow stream breaks up forming a monodispersion of bubbles of the gas in the second liquid.

21. The monodispersion of claim 20, wherein the bubbles are comprised of a gas selected from the group consisting of air, oxygen, and carbon dioxide, and wherein the liquid is aqueous.

22. The monodispersion of claim 20, wherein the gas is contaminated with a compound soluble in the liquid.

23. The monodispersion of claim 21, wherein the aqueous liquid is selected from the group consisting of water, sweetened water, and sewage.

24. The monodispersion of claim 20, wherein the bubbles are emitted at regularly spaced intervals from the exit orifice of the pressure chamber.

* * * * *